US00PP08721P

United States Patent [19]

Calder

[11] Patent Number: Plant 8,721

[45] Date of Patent: May 10, 1994

[54] SWEET CHERRY TREE NAMED 'REDLAC'

[76] Inventor: Donald A. Calder, 1301 O Ave., La Grande, Oreg. 97850

[21] Appl. No.: 819,372

[22] Filed: Jan. 8, 1992

[51] Int. Cl.[5] ..... A01H 5/00

[52] U.S. Cl. ..... Plt./37

[58] Field of Search ..... Plt. 37

[56] References Cited

PUBLICATIONS

Brooks, R. M., et al., "Rainier" *Register of New Fruit and Nut Varieties* 1972 University of California Press, Berkeley, p. 195.

*Primary Examiner*—James R. Feyrer
*Attorney, Agent, or Firm*—Klarquist, Sparkman, Campbell, Leigh & Whinston

[57] ABSTRACT

A new and distinct variety of sweet cherry tree, named 'Redlac' is disclosed, which is distinct from other commercial sweet cherry varieties as follows:

Large fruit borne in dense clusters having higher fruit count per cluster.

Fruit of larger scale than that of 'Erickson Lambert' and 'Rainier'.

Pollen which is self-fertile and cross-fertile with other commercial sweet cherry varieties.

Exceptionally frost and cold tolerance.

Produces fruit with deeper skin color than that of 'Erickson Lambert'.

Distinctive reddish bark on young limbs.

Larger leaves than comparison varieties.

Red coloration on leaf petioles.

The tree formed is of standard size and can be pruned to a tree having five scaffold branches to form a spreading, open centered tree.

5 Drawing Sheets

The present invention relates to a new and distinct variety of sweet cherry tree. I have named my new variety "Redlac".

In 1983, I purchased about one acre of land in La Grande, Ore., that was originally an orchard of various types of sweet cherry trees. Some of the trees were planted in the 1940s and others later. At the time I purchased the land, the cherry trees thereon had been badly neglected for many years.

I removed all the dead, dying, and badly damaged trees, leaving the following: four Rainiers, three Royal Anns, two Vans, and eight Erickson Lamberts. Identification of these remaining trees was aided at the time by the presence of nearly ripe fruit on all the trees. I also consulted with a local, highly respected botanist familiar with the trees on my land and with regional cherry production in general dating back to the 1940's.

As suggested by the botanist, I extensively pruned all the remaining trees to reduce their size and to stimulate fresh vegetative growth and fruit production.

The following spring, vigorous new growth had begun on all the remaining trees, including an Erickson Lambert tree referred to herein as the "mother tree."

Since the pollinating trees (Vans and Rainiers) on my property were located remotely from the Erickson Lambert trees (which are not pollinators), I needed to take some action to augment pollination of the Erickson Lambert trees. I first considered procuring several young Van trees for planting near the Erickson Lambert trees. But, I did not want any more Vans because Van cherries have poor marketability in my locale.

I therefore decided to try a grafting experiment. Since Rainier was a pollinator variety, I removed two vegetative buds from a limb of new (one-year) growth on one of the Rainier trees about 200 feet away from the mother tree. This "source limb" originated about five feet from the ground from a major branch (exhibiting Rainier characteristics) on the Rainier tree. The two buds were grafted, via "T-budding" as known in the art, to a stock limb of vigorous new growth on the mother tree having diameter of about one inch and a length of about five feet. The stock limb arose from Erickson Lambert wood about five feet from the ground.

Each of the two grafted buds survived and grew. In fact, no growth from indigenous buds occurred on the stock limb and no other buds were grafted to it.

Unfortunately, the source limb on the Rainier tree was accidentally killed a short time later by a neighbor shooting a shotgun into the tree in an attempt to scare away marauding birds. In any event, this tree (including all other growth originating at five feet from the ground) was positively identified as a Rainier variety independently by three different skilled horticulturists.

The exact age of the Rainier tree that provided the buds is not known. However, the irregular positions of the Rainier trees on my property relative to the other cherry trees suggest that the Rainiers were planted later than the others, probably in the early 1960s.

During the spring after grafting the two buds to the sport limb, the portion of the sport limb distal to the bud grafts was pruned away to stimulate vigorous growth from the bud grafts.

In 1986, the growth from the bud grafts produced a handful of cherries. Since the grafts were obtained from a Rainier tree, I fully expected the cherries produced on the growth to exhibit Rainier characteristics: relatively small, deep yellow cherries with a reddish blush when fully ripe. To my surprise, the cherries were all very large and dark reddish purple when fully ripe.

The genotype of growth developing from grafted buds is determined by the genotype of the tissue that generated the buds. Thus, the two buds grafted to the stock limb on the mother three must have been removed from a sport limb on the Rainier tree. But, at the time I made the grafts, it was not apparent to me that the source limb was a sport limb. Also, as described above, the source limb was unfortunately accidentally destroyed before its unique qualities became known.

The growth from each grafted bud on the stock limb on the mother tree represents a first-generation growth of my new "Redlac" variety of cherry.

The first-generation Redlac cherries had the following characteristics as distinguished from the Erickson Lambert cherries produced on my property: the Redlac cherries were slightly rounder than Erickson Lambert cherries and had stems about the same length as Erickson Lambert cherries. Also, the pits of the Redlac cherries were slightly smaller than Erickson Lambert pits. The ripe Redlac cherries had deep reddish purple skins, slightly darker than ripe Erickson Lambert cherries. Although I did not determine a size distribution for this first crop of Redlac cherries, the Redlac cherries appeared to be generally substantially larger than Erickson Lambert cherries. The Redlac cherries were also produced in more numerous, larger, and more closely spaced clusters than the Erickson Lambert cherries. Finally, the flesh of the Redlac cherry had a similar texture to the Erickson Lambert cherry, but was lighter in color than the Erickson Lambert flesh and slightly darker than the Rainier flesh.

Turning now to a comparison of the first-generation Redlac cherries with other varieties of cherries produced on my property, the Rainier cherries were medium to large in size, but were definitely smaller than the Redlac cherries. Like Rainier cherries, the Redlac cherries had long stems. The most notable difference, however, was that the Rainier cherries were yellow-skinned with a reddish blush, not deep reddish purple. Thus, the Redlac cherries were readily distinguishable from Rainier cherries. The Van cherries were medium-sized round cherries, smaller than Redlac cherries, and with much shorter stems than Redlac cherries. Also, the Van cherries had purplish black skins that were substantially darker than Redlac cherries. The Royal Ann cherries were much smaller and had shorter stems than Redlac cherries. Also, the Royal Ann cherries were oval rather than round and were yellow-pink in color rather than reddish purple.

With respect to vegetative characteristics, the Redlac limbs had a distinctive reddish bark in contrast to the grayish bark found on Erickson Lambert and Rainier limbs of about the same age. Also, the Redlac leaves were slightly larger than Erickson Lambert and Rainier leaves and had more pronounced serrations on the edges than Erickson Lambert and Rainier leaves. The Redlac leaves also had a distinctive red coloration on dorsal surfaces of the petioles in contrast to the completely green petioles found on Erickson Lambert and Rainier leaves.

It was not incredible, in retrospect, that the Redlac cherries were dark skinned, despite the fact that the grafted buds were removed from a limb on a Rainier tree which produces light-skinned cherries. It will be recalled that the yellow-skinned Rainier cherry originated from a cross of two dark-skinned varieties: Bing and Van.

In the winter of 1986–1987, the cherry crop throughout the Grande Rhonde valley in which my property was located was badly damaged by severely cold weather. Many trees in the general area produced little to no fruit. The Erickson Lambert, Van, Royal Ann, and Rainier trees on my property were similarly damaged. The Redlac growth on the mother tree, in contrast, experienced relatively little damage and produced about twenty pounds of cherries. Thus, the Redlac growth apparently had a significantly enhanced tolerance to cold and frost relative to the other varieties of cherry trees on my property and relative to cherry trees elsewhere in the Grande Rhonde valley.

In the spring of 1988, four scions from the first-generation Redlac growth were grafted onto separate Mazard root stocks so as to asexually produce second-generation Redlac trees. All these grafts survived and grew.

Also, by that spring, the first-generation Redlac limbs that grew from the two bud grafts had fully developed and were quite effective as pollinators of themselves, of the Erickson Lambert mother tree, and of other nearby Erickson Lambert trees. The mother tree, which previously produced only about 100 to 125 pounds of cherries per season, produced in the spring of 1988 over 600 pounds of cherries, of which about 100 pounds were Redlac cherries. (The Redlac growth represented a minor proportion of the total mass of fruit-producing growth on the tree. I.e., most of the growth was Erickson Lambert growth.) Two Erickson Lambert trees nearest the mother tree experienced a two-fold increase in production. More distinct Erickson Lambert trees did not exhibit significant increases in fruit production over their normal production levels.

In the spring of 1988, the cherries produced by the first-generation Redlac growth were again readily distinguishable from all the other cherries produced on my property according to the distinctive characteristics discussed above, namely fruit size and color, stem length, pit size, and abundance of fruit produced per unit length of stem.

To quantify the size of the Redlac cherries I removed a random five-pound sample of cherries from one of the first-generation Redlac limbs and sized them as follows using the black-cherry scale:

1 cherry: 12 row
44 cherries: 11 row
177 cherries: 10 row
10 cherries: 9 row

Thus, these Redlac cherries had a median size of about 10 row.

In contrast, the Erickson cherries had a median size of only about 12 row (wherein 12 row is smaller than 9, 10, or 11 row). Cherries produced by Rainier trees in my orchard had a median size of 11 row on the black-cherry scale, which was slightly larger for this variety. Thus, the Redlac cherries were even larger than Rainier cherries.

In 1989, I removed five scions from the second-generation Redlac trees and grafted them onto separate Mazard root stocks to produce third-generation Redlac trees. All these grafts survived and grew.

Meanwhile, the Redlac growth on the mother tree continued to produce extraordinarily large clusters of cherries. This Redlac growth also effectively and heavily pollinated itself, the mother tree, and surrounding Erickson Lambert trees.

In 1990, two of the four second-generation Redlac trees began producing cherries having characteristics identical to cherries produced by the first-generation Redlac growth. In addition, all the second-generation Redlac trees exhibited the same distinctive reddish bark, large leaves with pronounced serrations, and red petioles as the first-generation Redlac growth.

In the winter of 1990–1991, the weather was again very severe, killing or severely damaging a number of orchard and decorative trees in the area. On our property, one old Royal Ann tree was killed and the remaining two Royal Ann trees suffered severe vegetative and fruiting damage. The Van trees also suffered severe vegetative damage and total loss of flowering and fruit production for that year. The Erickson Lambert trees also suffered substantial damage to vegetative buds and some damage to fruiting buds. The four Rainier trees suffered only light vegetative damage, but complete loss of fruiting buds for the year. However, no vegetative or fruiting damage occurred to the original Redlac growth on the mother tree, the four second-generation Redlac trees, or the five third-generation Redlac trees.

Since the severe weather destroyed the fruiting buds on the Van and Rainier trees, they produced no pollen that could have pollinated the Redlac growth or the Erickson Lambert trees. Nevertheless, all eight of the Erickson Lambert trees (which are not self-pollinators) produced cherries. The two Erickson Lambert trees closest to the mother tree produced about a ten-percent normal crop of cherries; the Erickson Lambert growth on the mother tree produced about a forty-percent yield, and the Redlac growth on the mother tree about a seventh-percent yield. These observations again indicate that my Redlac variety has exceptional frost and freezing tolerance as well as good pollinating ability.

In an experiment to determine how well the Redlac cherry tolerates other climates and elevations, scions from the first-generation Redlac growth were grafted onto cherry tree stocks in the following locations:

| | |
|---|---|
| Red Bluff, CA | (300-ft elev, very hot, early season) |
| La Grande, OR | (2800-ft elev, cool) |
| Laytonville, CA | (1600-ft elev, hot summer, cold winter) |
| Arcata, CA | (sea level, cool summers) |
| The Dalles, OR | (400-ft elev, hot summers) |

Also, scions from the second-generation Redlac trees were whip-grafted onto Mazard root stocks and placed at a location in Elgin, Ore., characterized by a 3300 foot elevation and extremely cold winters. The grafts were placed about five miles from the nearest cherry tree. Other similar grafts were placed in Hermiston, Ore., at 500 feet elevation and characterized by a very warm climate and early season.

Scions from second-generation Redlac trees were also experimentally grafted onto Colt root stock and placed at a location in Fort Bragg, Calif., at 200 feet elevation with a mild, damp, foggy climate.

Only the grafts placed at Red Bluff and La Grande have produced any fruit to date. These grafts exhibited the typical characteristics of the new Redlac variety; namely, unusually large cherries borne in large, dense clusters, small pits, long stems, deep red-purple color, and self-pollination ability. In addition, the leaves and bark of vegetative growth from the grafts exhibited the distinctive Redlac vegetative characteristics discussed above.

Close observation of the original Redlac bud sports, as well as of second- and third-generation asexually produced progeny thereof, confirmed that the unique characteristics of my new variety of cherry are indeed different from other varieties of cherries of which I am aware. The above-named unique characteristics have been repeatedly observed in the original Redlac bud sports as well as second- and third-generation asexual progeny thereof to be identical, one to the next. Therefore, I am convinced that my new variety of cherry represents a new and improved variety of sweet cherry tree, as particularly evidenced by the following unique combination of characteristics, which have proven firmly fixed and are outstanding therein, and which distinguish the Redlac cherry from other varieties of this species:

1. produces cherries borne in dense grapelike clusters that are larger, more dense, and have more cherries per cluster than clusters produced by other varieties of cherries of which I am aware;
2. produces cherries that are larger than Erickson Lambert or Rainier varieties;
3. excellent pollinator of itself and other cherry trees;
4. exceptional tolerance to cold and frost relative to other cherry trees of which I am aware;
5. produces cherries having a deeper red-purple skin color than Erickson Lambert cherries and that are readily distinguished from the yellowish cherries of the Rainier variety;
6. distinctive, reddish bark on young limbs;
7. large leaves with more pronounced serrations than Erickson Lambert, Van, Rainier, Royal Ann leaves; and
8. red petioles on the leaves.

The accompanying photographs depict the color of the fruit and other parts of my new cherry variety as nearly true as is reasonably possible to make the same in color illustrations of this character.

FIG. 2 is a color photograph taken in 1991 showing limbs on the Redlac first-generation growth, which exhibit reddish bark and general shape and color of leaves.

FIG. 3 is a color photograph taken about ten days after picking, showing on the left a typical ten-row sized Redlac cherry (obtained from the first-generation Redlac growth) and on the right a typical twelve-row sized cherry from the Erickson Lambert mother tree. (The template is conventionally used for sizing cherries and is included in the photograph for reference purposes.) Thus, it can be readily seen that the Redlac cherries are larger and rounder than the heart-shaped Erickson Lambert cherries.

Figure 1:
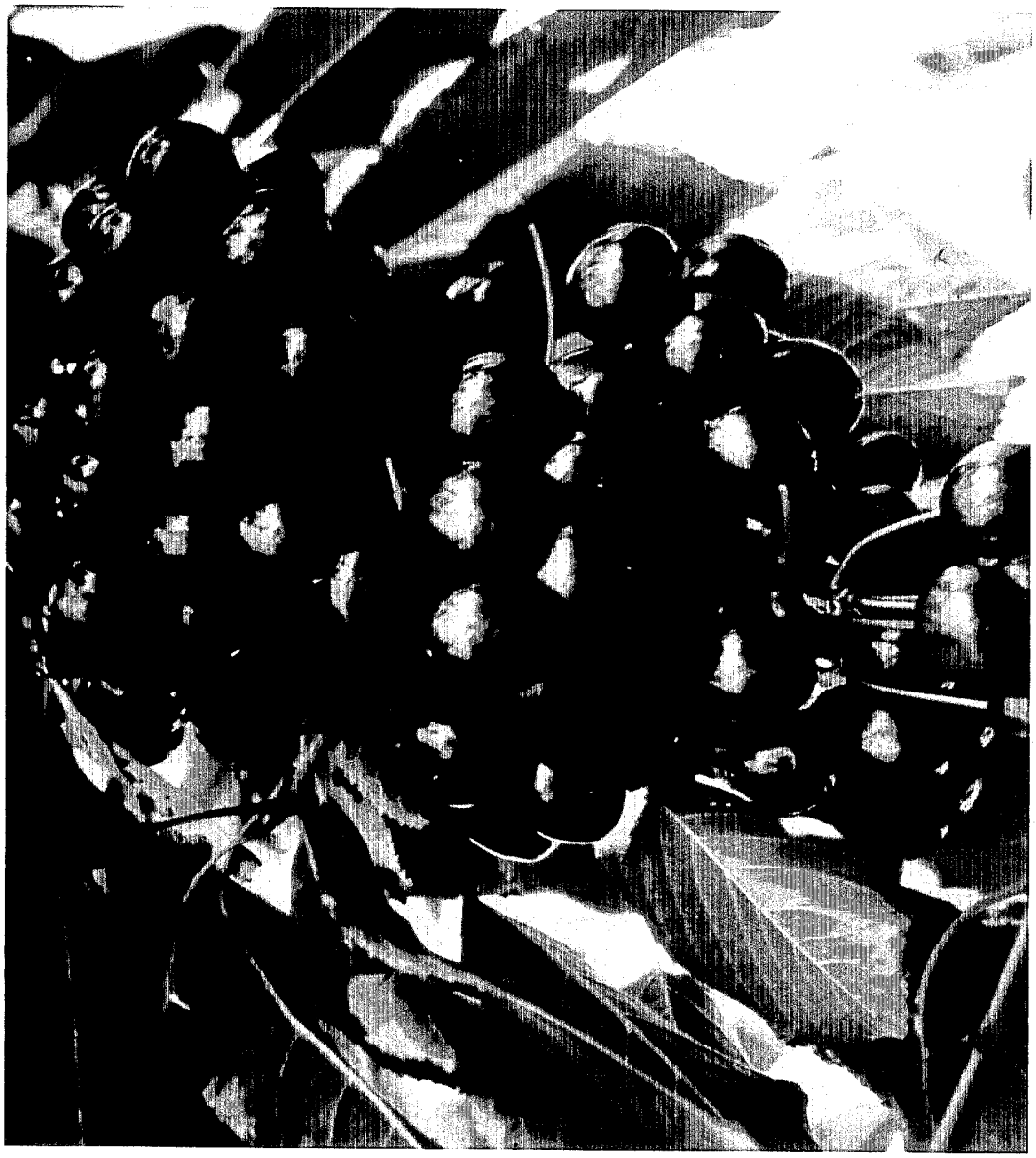
FIG. 1 is a color photograph taken in 1988 of a cluster of cherries produced by the Redlac first-generation growth on the mother tree. The tendency to produce abundant fruit from unusually closely spaced spurs is evident.
Figure 4:
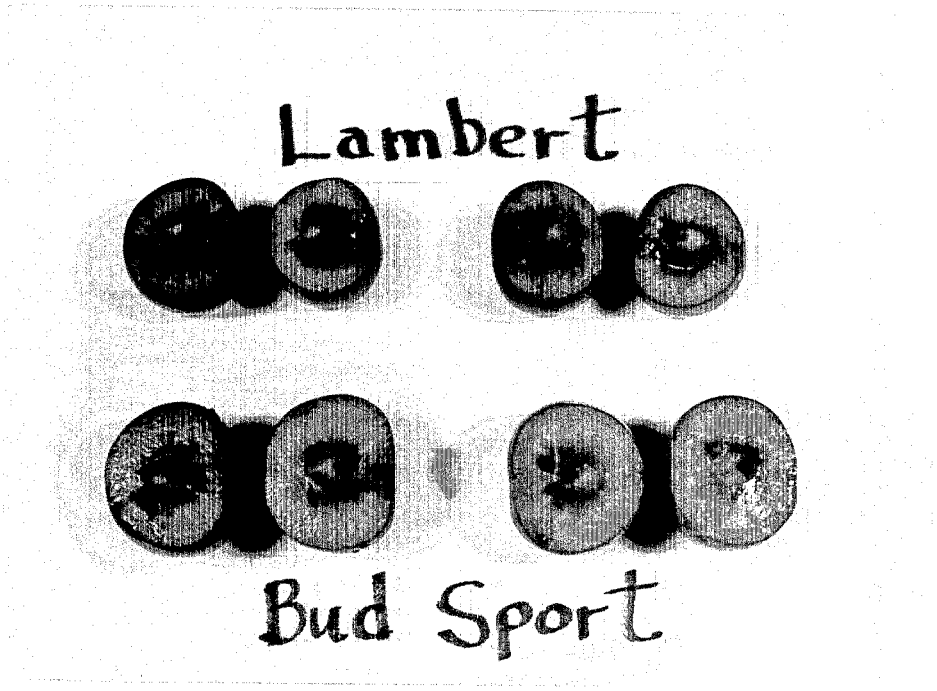

FIG. 4 shows four sliced Erickson Lambert cherries in the top row and four sliced Redlac cherries (labeled "Bud Sport") in the bottom row. Again, the substantially larger fruit of the Redlac cherry is readily evident. The pits of the Redlac cherries, however, are no larger than the pits of Erickson Lambert cherries, indicating that the Redlac cherries contain more edible fruit per cherry. FIG. 4 also shows that the flesh of the Redlac cherry is lighter in color than the flesh of Erickson Lambert cherries.

Figure 5:
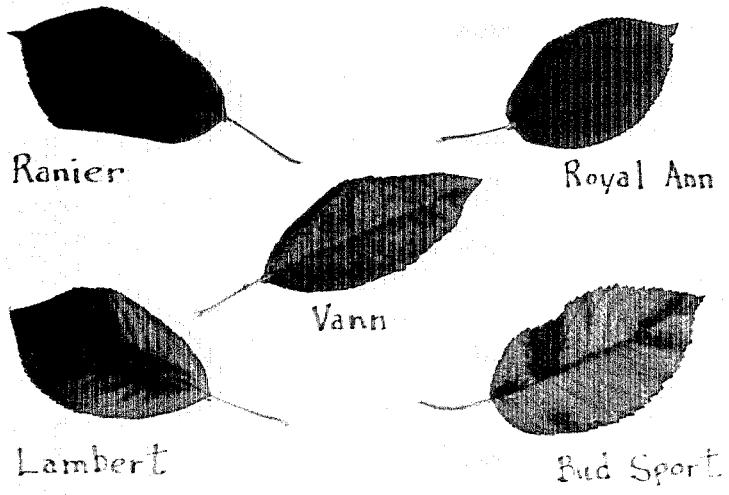

FIG. 5 shows, for comparison purposes, dorsal surfaces of representative leaves from Rainier, Royal Ann, Van, Erickson Lambert, and the first-generation Redlac (labeled "Bud Sport") varieties. The Redlac leaves have about the same shape but are slightly larger than leaves of the other varieties shown. The Redlac leaf margin has more pronounced serrations and red coloration on the dorsal petiole surface.

Figure 6:
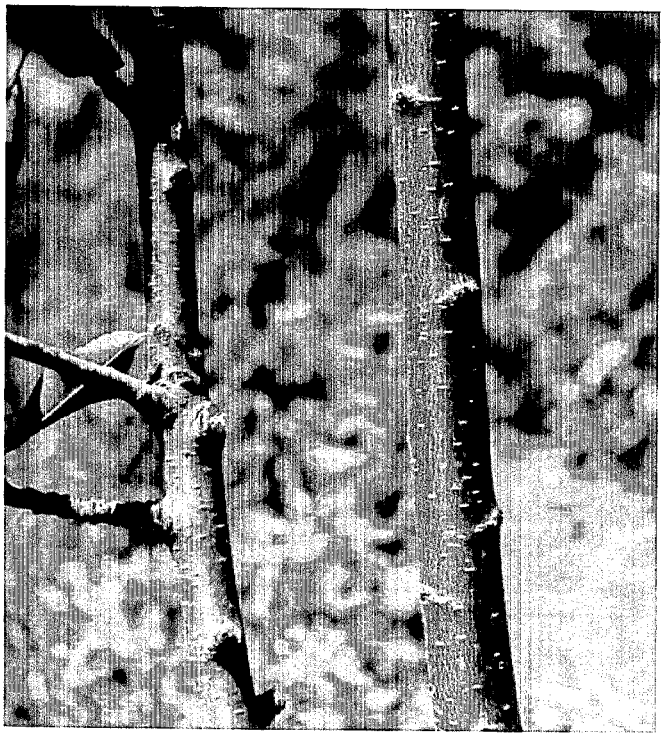

FIG. 6 shows, for comparison purposes, a second-year Erickson Lambert limb from the mother tree (left) and a Redlac limb of the same age (right), exhibiting the distinctive reddish bark of new-growth bark on Redlac limbs and the grayish new-growth bark on Erickson Lambert limbs. Also evident are the abundant and pronounced lenticels on the Redlac limb (about as abundant as on Erickson Lambert limbs) which contrast strongly with the reddish bark.

Figure 7:
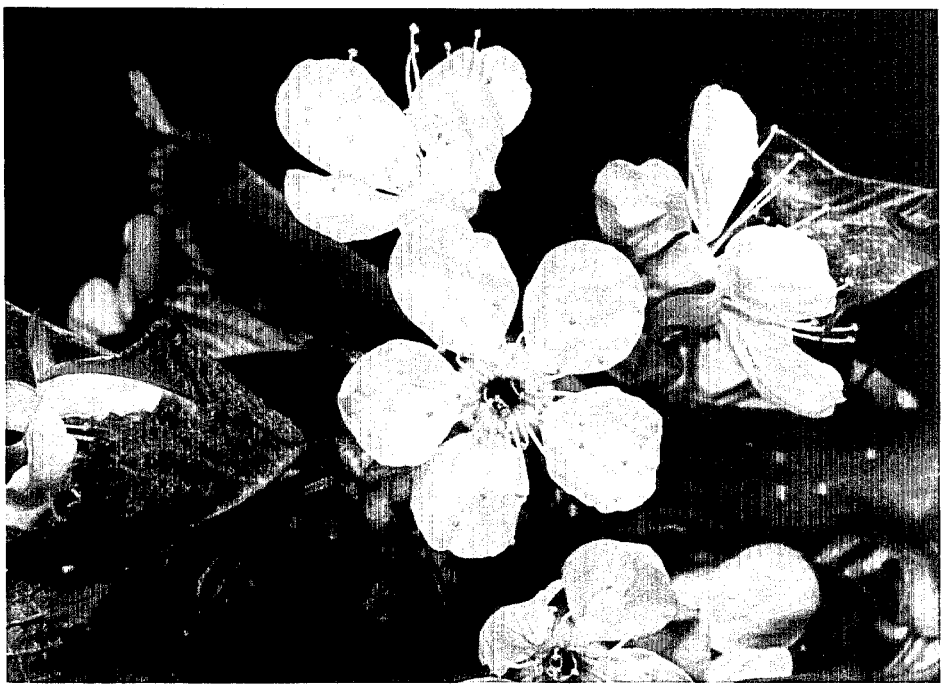

FIG. 7 is a close-up photograph of several Redlac blooms showing the white petals, yellow stamens, and green sepals.

Figure 8:
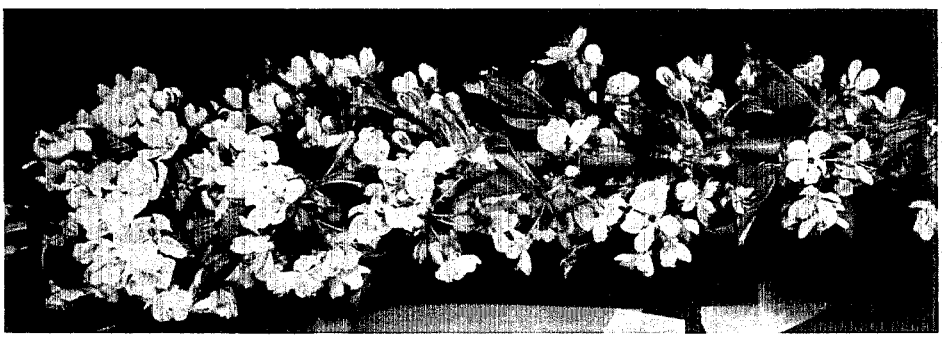

FIG. 8 shows a Redlac flowering limb exhibiting dense production of blooms from unusually closely spaced spurs.

Figure 9:
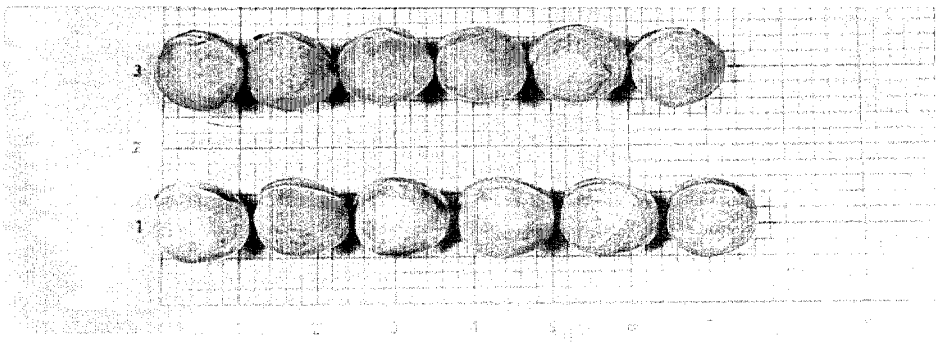

FIG. 9 shows, on the upper line, a random selection of six Redlac pits arranged end to end and, on the lower line, a random selection of six Erickson Lambert pits similarly arranged, showing that the Redlac pits are slightly smaller than (certainly no larger than) Erickson Lambert pits.

The following is a detailed botanical description of my new variety of cherry tree, wherein colors are designated by reference to The Royal Horticultural Society (London) Colour Chart.

Genus and species: *Prunus avium,* L. (sweet cherry).

Variety: "Redlac".

Parentage: vegetative buds from what was apparently a sport limb (now destroyed) on a Rainier variety of sweet cherry tree (that had previously been heavily pruned to stimulate new growth) T-bud grafted onto a limb of vigorous new growth on an Erickson Lambert tree.

Locality where first growth and observed: La Grande, Ore.

Tree:

*Size.*—Appears to be "standard" sized as opposed to dwarf or semi-dwarf.

*Vigor.*—Exceptional cold and frost tolerance compared to Erickson Lambert, Rainier, Van, and Royal Ann sweet cherry trees. Excellent self-pollinator; also pollinates Erickson Lambert trees. Second- and third-generation trees have been experiencing about five feet of vegetative growth per year.

*Habit.*—Young trees are normally pruned to maintain no more than five lateral main limbs. This tends to facilitate development of a spreading, open-centered tree.

*Fruit distribution.*—From clusters on lateral spurs.

*Bark.*—Distinctly reddish, smooth, and glossy on young wood; becoming deeper in color and ultimately grayer as bark thickens on mature wood. Color: Three-year old limb: greyed-orange group 175B; Seven-year old limb: greyed-orange group 175A.

*Branches.*—Primary distribution.

*Lenticels.*—Pronounced, particularly on young bark, oriented laterally relative to the stem axis. Shape: oblong to linear. On a typical region on a three-year old limb having a length of 8 cm and circumference of 4 cm, 72 lenticels were present ranging from 0.3 to 2.5 mm long (with a mean length of 1.5 mm and mean width of 1 mm). Color of lenticels on three-year old wood: yellow-white group 158D. On a typical region on a seven-year old limb having a length of 8 cm and a circumference of 13.1 cm, 135 lenticels were present ranging from 1.5 to 7 mm in length (mean length of 4 mm and mean width of 2 mm). Color of lenticels on seven-year old wood: yellow-white group 158A. On a typical 8×4 cm region on a ten-year old limb (measuring 9.5 cm in diameter) normally shaded from sunlight, 34 lenticels were present ranging from 3 mm to 11.5 mm long (mean length=6 mm) and 3 mm width. Color of these ten-year old lenticels was orange-white group 159B.

*Leaves.*—Leaf shape generally oblong-elongate, usually oblong-ovate to oblong-obovate; gradually taper-pointed. Leaf blade 7.6 cm (3 inches) to about 13 cm (5 inches) long (about the same length as to slightly longer than Erickson Lambert leaves), soft in texture, hanging limp on young growths. Margins serrated; with more pronounced serrations than on Erickson Lambert leaves.

*Color of new leaves in full sunlight.*—Yellow-green group 144A on top, yellow-green group 146B on bottom. Color of medium-aged leaves in full sunlight: yellow-green group 147A on top, yellow-green group 147B on bottom. Color of old mature leaves in full sunlight: green group 137A on top, yellow-green group 147B on bottom. Petioles of both new and old leaves have reddish dorsal surfaces and green ventral surfaces. Red color normally extends along entire length of the petiole, but not along central vein of leaf. Color of red dorsal surface: greyed-orange group 176B. Color of green ventral surface of petiole: yellow-green group 144A.

*Glands.*—Normally present on petioles. On most leaves, glands are located about 2 mm below the leaf base, with a mean number of two glands (range 1–4) per leaf, each gland being oblong in shape and oriented about parallel to the petiole. Glands have a mean 1 mm width and 2 mm length. Gland color on new leaves in full sunlight: greyed-red group 181A. Gland color on medium-aged leaves in full sunlight: greyed-orange group 172C. Gland color on old, mature leaves in full sunlight: greyed-orange group 172B. In contrast, glands on Rainier leaves are smaller (averaging 0.5 mm diameter), round in shape rather than oblong, located at the leaf base, and have a greyed-red group 178B color. Glands on Royal Ann leaves are round (mean diameter of 1 mm), located at the base of the leaf, and have a greyed-red group 178C color. Glands on the Van leaves are located at the leaf base, are round in shape (mean diameter of 1 mm), and have a greyed-red 178C color. Glands on the Erickson-Lambert leaves are round, about 0.5–1.0 mm in diameter, and mostly located on the petiole at the leaf base. However, a substantial number of glands appear on the edge of the leaf blade near the petiole. Color of glands on new Erickson-Lambert leaves: yellow-orange group 19A; color on medium-aged leaves: orange group 26B; and color on old mature leaves: orange-red group 34C.

Flowers: About the same size and color and borne in the same general manner as Erickson Lambert flowers, but in denser clusters than Erickson Lambert flowers.

*Petals.*—Pure white, occasionally with reddish or purple veins; five per flower.

*Stamens.*—Yellow, becoming darker with age of the flower.

*Sepals.*—Green.

*Blooming period.*—In LaGrande, Ore., during normal weather for this location, flower buds on the Redlac cherry reach the "popcorn" stage about 2–4 days after Erickson Lambert, and about 6–9 days after Van, Rainier, and Royal Ann. For example, at LaGrande, Ore., in the spring of 1993, the Van, Rainier and Royal Ann varieties developed "popcorn"-stage buds on April 26, the Erickson Lambert on April 30, and Redlac on May 2. Full bloom on Redlac trees normally occurs about 5–7 days after the "popcorn" stage. The spring of 1993 was unusually cool and wet in LaGrande, Ore., resulting in all the foregoing varieties reaching full bloom simultaneously on May 7. By May 12, all the foregoing varieties exhibited petal drop, and on May 15, little new cherries were visible. Pollination was particularly heavy. It is expected that other locations and/or weather conditions other than those prevailing at LaGrande, Ore., or use of growth regulators, would result in an earlier or later blooming period than described above.

Fruit:

*Color.*—Deep purple skins when fully ripe on the tree, with red showing from beneath skin in full sunlight. Color varies somewhat from cherry to cherry but greyed-purple group 187A is the typical color in full sunlight.

*Shape.*—Nearly round, similar to the shape of Rainier cherries; less pointed than Lambert cherries.

*Size.*—Mostly ten row, generally ranging from 9 to 12 row (on black cherry scale).

*Surface.*—Smooth; glossy.

*Flesh.*—Firm texture; flesh is red, lighter in color than in Erickson Lambert cherries and slightly darker in color than in Rainier cherries. Fibers are whitish, few in number, and tender. Very juicy flesh, with red juice color. When compared to Van, Royal Ann and Erickson Lambert cherries during wet conditions prevailing on a given date, ripening fruit of the Redlac cherry appears to be less susceptible to splitting.

*Pit.*—Small in size, about the same shape as, and no larger than, pits in Erickson Lambert and Rainier cherries. Pit is semi-free, not quite as free as pits in Erickson Lambers and Rainier cherries.

*Stems.*—About 6.4 cm (2½ inches) long; about the same length as Erickson Lambert.

*Ripening.*—During normal weather conditions at LaGrande, Ore., and without the use of growth regulating substances, Van and Royal Ann cherries are harvested on about July 8th–10th; Rainier cherries about 4–5 days later; Erickson Lambert cherries about 2–3 days Rainier cherries; and Redlac cherries about 2–3 days after Erickson Lambert cherries. It is expected that weather conditions other than those prevailing at LaGrande, Ore., or growth in locations other than LaGrande, Ore., or use of growth regulators, could significantly change the harvest date of Redlac cherries (and other varieties of cherries). For example, July of 1993 at LaGrande, Ore., was unusually cool and wet, causing a harvest delay of 10–12 days for all the foregoing varieties, including Redlac. The relative dates of harvest, however, remained substantially the same for these varieties. The fruits of this cherry tend to ripen substantially uniformly under identical conditions. Individual fruits that are mostly shaded from full sunlight tend to reach a fully ripe condition a day or two later than fruits that are exposed to sunlight for substantial periods during the day.

*Shelf life.*—Refrigerated: 3–4 weeks.

*Sweetness.*—Medium to very sweet, much like Erickson Lambert.

Disease resistance: Non susceptibility to plant diseases, including brown rot or cherry yellow-leaf disease, has been observed with this variety. There is no known susceptibility to pests.

Ploidy: Unknown; believed to be normal ploidy (diploid) based upon apparent great fertility of pollen and upon pollination ability of this variety both of itself and nearby Erickson Lambert varieties.

Other characteristics: Redlac cherries are excellent for canning, drying and freezing.

I claim:

1. A new and distinct variety of cherry tree, substantially as herein shown and described.

* * * * *

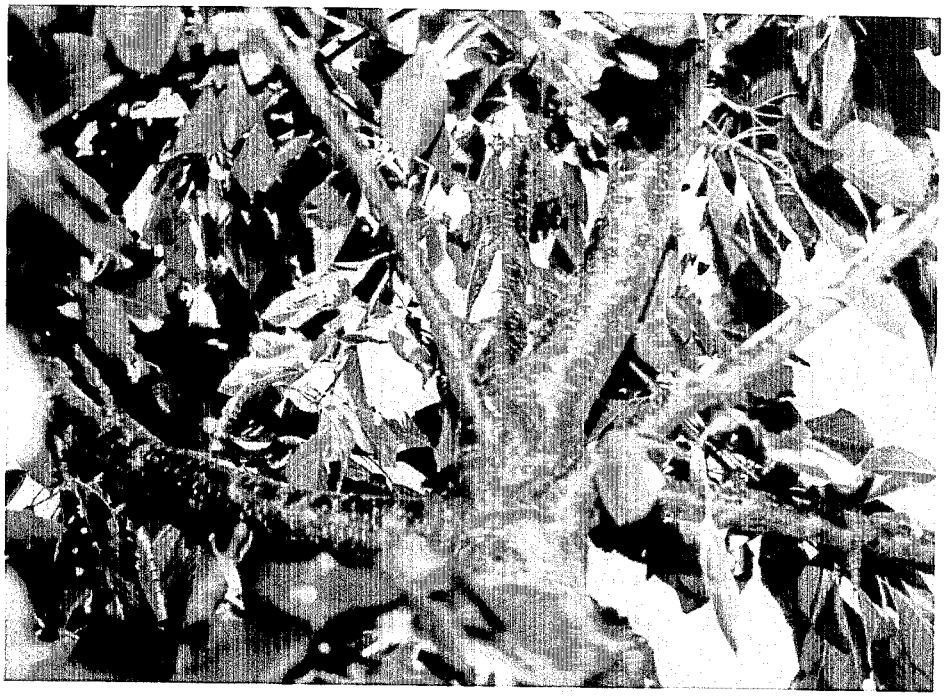
FIG. 2
FIG. 3
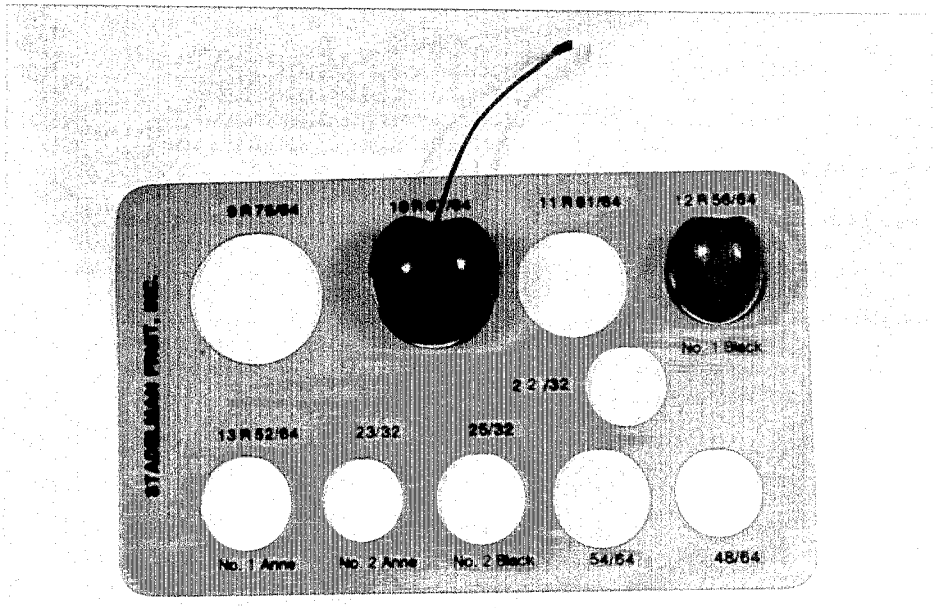

UNITED STATES PATENT AND TRADEMARK OFFICE

CERTIFICATE OF CORRECTION

PATENT NO. : PP 8,721

DATED : May 10, 1994

INVENTOR(S) : DONALD A. CALDER

It is certified that error appears in the above-identified patent and that said Letters Patent is hereby corrected as shown below:

Column 4, line 50, "larger" should be --large--.

Column 8, line 11, "width" should be --wide--.

Column 10, line 6, "Lambers" should be --Lambert--.

Column 10, line 14, "days Rainier" should be --days after Rainier--.

Column 10, line 37, "non" should be --No--.

Signed and Sealed this

Twenty-ninth Day of November, 1994

Bruce Lehman

*Attest:*

BRUCE LEHMAN

*Attesting Officer*

*Commissioner of Patents and Trademarks*